US010031063B2

(12) United States Patent
Tahara

(10) Patent No.: US 10,031,063 B2
(45) Date of Patent: Jul. 24, 2018

(54) PARTICLE ANALYSIS APPARATUS AND METHOD FOR OPTICALLY DETECTING PARTICLES

(71) Applicant: SONY CORPORATION, Tokyo (JP)

(72) Inventor: Katsutoshi Tahara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 96 days.

(21) Appl. No.: 14/905,823

(22) PCT Filed: Jun. 6, 2014

(86) PCT No.: PCT/JP2014/065136
§ 371 (c)(1),
(2) Date: Jan. 17, 2016

(87) PCT Pub. No.: WO2015/012004
PCT Pub. Date: Jan. 29, 2015

(65) Prior Publication Data

US 2016/0161393 A1 Jun. 9, 2016

(30) Foreign Application Priority Data

Jul. 23, 2013 (JP) ................................ 2013-152176

(51) Int. Cl.
*G01N 15/14* (2006.01)
*G01N 21/53* (2006.01)
*G01N 21/64* (2006.01)

(52) U.S. Cl.
CPC ..... *G01N 15/1429* (2013.01); *G01N 15/1434* (2013.01); *G01N 15/1459* (2013.01);
(Continued)

(58) Field of Classification Search
CPC . G01N 21/00; G01N 15/1429; G01N 15/1434
(Continued)

(56) References Cited

U.S. PATENT DOCUMENTS 5,247,339 A * 9/1993 Ogino ................ G01N 15/1463
250/461.2
5,504,337 A * 4/1996 Lakowicz .......... G01N 15/1434
250/459.1
(Continued)

FOREIGN PATENT DOCUMENTS

JP SHO 61-038447 A 2/1986
JP SHO 62-003642 A 1/1987
(Continued)

*Primary Examiner* — Roy M Punnoose
(74) *Attorney, Agent, or Firm* — Chip Law Group

(57) ABSTRACT

A particle analysis apparatus and a particle analysis method capable of acquiring detection data with high reliability without performing high frequency superimposition. A particle analysis apparatus to includes: a light irradiation unit that irradiates particles flowing within a flow path with laser light; a light detection unit that detects at least one of fluorescence light or scattered light and a signal processing unit that processes a detection signal of at least one of the fluorescence or the scattered the light irradiation unit including at least a light source that generates laser, and a laser light detector that detects part of laser light emitted from the light source, the signal processing unit correcting the detection signal of the fluorescence or the scattered light or the detection signals of both the fluorescence and the scattered light, based on a detection result and output fluctuations in the laser light detector.

6 Claims, 3 Drawing Sheets

(52) U.S. Cl.
CPC ........... *G01N 21/53* (2013.01); *G01N 21/645* (2013.01); *G01N 2021/6491* (2013.01)

(58) Field of Classification Search
USPC .......................................................... 356/338
See application file for complete search history.

(56) References Cited

U.S. PATENT DOCUMENTS

| | | | | |
|---|---|---|---|---|
| 7,822,558 | B2 * | 10/2010 | Kimura | G01N 21/274 356/32 |
| 8,415,627 | B2 * | 4/2013 | Doi | G01N 15/1429 250/354.1 |
| 2004/0011975 | A1 * | 1/2004 | Nicoli | G01N 15/0227 250/574 |
| 2004/0189977 | A1 * | 9/2004 | Nagai | G01N 15/1459 356/39 |
| 2005/0002826 | A1 * | 1/2005 | Oguni | G01N 33/5094 422/73 |
| 2009/0108214 | A1 * | 4/2009 | Shinoda | G01N 15/1425 250/492.1 |
| 2009/0116005 | A1 * | 5/2009 | Furuki | G01N 15/1425 356/246 |
| 2011/0168916 | A1 * | 7/2011 | Doi | G01N 15/1429 250/459.1 |

FOREIGN PATENT DOCUMENTS

| | | | |
|---|---|---|---|
| JP | SHO 62-162946 | A | 7/1987 |
| JP | SHO 63-024139 | A | 2/1988 |
| JP | HEI 03-200050 | A | 9/1991 |
| JP | HEI 04-058137 | A | 2/1992 |
| JP | HEI 04-127033 | A | 4/1992 |
| JP | HEI 04-232442 | A | 8/1992 |
| JP | HEI 06-094596 | A | 4/1994 |
| JP | HEI 09-178645 | A | 7/1997 |
| JP | 2009-053020 | A | 3/2009 |
| JP | 2012-073070 | A | 4/2012 |

* cited by examiner

PARTICLE ANALYSIS APPARATUS AND METHOD FOR OPTICALLY DETECTING PARTICLES

TECHNICAL FIELD

The present technology relates to a particle analysis apparatus and a particle analysis method for optically detecting particles. More particularly, the present technology relates to a technology to improve detection accuracy in a particle analysis apparatus and a particle analysis method for detecting fluorescence or scattered light that is emitted from particles irradiated with light.

BACKGROUND ART

For discrimination of biologically-relevant microparticles such as cells, microbes, and liposomes, an optical detection method using flow cytometry (flow cytometer) is used. The flow cytometry is an analytical technique to irradiate particles flowing in line within a flow path with laser light of a specific wavelength and detect fluorescence or scattered light emitted from each of the particles, to discriminate the particles from one another.

Meanwhile, in the flow cytometry, an oscillation wavelength of a laser fluctuates in the order of several tens of μs due to the influences of the flow path, return light from the particles, and the like. This causes a change in the amount of light output from the laser, and this change is detected as noise. Such noise is generally called "mode hopping noise" and becomes a cause of variations in detection data or of a reduction in reliability.

The flow cytometry is provided with a laser output adjustment system (auto power control: APC) in order to prevent a laser output level from fluctuating due to the influence of temperature or the like. However, feedback control by the APC is performed in the order of several ms and cannot cope with mode hopping noise that occurs in the order of several tens of μs.

In the past, the use of high frequency superimposition has been proposed as a method of reducing the mode hopping noise and making the laser output stable (see Patent Document 1). For example, in a sample analyzer described in Patent Document 1, a high-frequency superimposition circuit that superimposes a high-frequency component on a direct current supplied to a laser diode is provided, and the amplitude of the high-frequency wave superimposed on the direct current is controlled in accordance with the magnitude of the direct current supplied to the laser diode.

Patent Document 1: Japanese Patent Application Laid-open No. 2009-53020

SUMMARY OF INVENTION

Problem to be Solved by the Invention

However, a laser output stabilizing technology using the high frequency superimposition requires high speed blinking of the laser in order to improve the effects. As a result, peak output is increased, and it becomes necessary to use a laser whose maximum output rating is high, to reduce average output, and the like. Further, in such a case, the amplitude of the high frequency superimposition is increased, and thus unnecessary radiation is also increased.

In this regard, it is a main object of the present disclosure to provide a particle analysis apparatus and a particle analysis method that are capable of acquiring detection data with high reliability without using high frequency superimposition.

Means for Solving the Problem

According to the present disclosure, there is provided a particle analysis apparatus including: a light irradiation unit that irradiates particles flowing within a flow path with laser light; a light detection unit that detects fluorescence or scattered light or both the fluorescence and the scattered light, the fluorescence and the scattered light being emitted from the particles irradiated with the laser light; and a signal processing unit that processes a detection signal of the fluorescence or the scattered light or detection signals of both the fluorescence and the scattered light, the fluorescence and the scattered light being output from the light detection unit, the light irradiation unit including at least a light source that generates laser, and a laser light detector that detects part of laser light emitted from the light source, the signal processing unit correcting the detection signal of the fluorescence or the scattered light or the detection signals of both the fluorescence and the scattered light, based on a detection result in the laser light detector.

The signal processing unit may correct the detection signal or the detection signals in accordance with output fluctuations of the laser light detector.

In such a case, the signal processing unit may correct the detection signal or the detection signals by multiplying an output voltage from the light detection unit by a value (Gain) that is set in accordance with magnitude of the output fluctuations of the laser light detector.

On the other hand, the light irradiation unit may include a beam splitter that reflects the part of the laser light toward the laser light detector.

Further, the light irradiation unit may also include a light source drive control unit that adjusts output of laser light based on a detection result in the laser light detector, the laser light being output from the light source.

According to the present disclosure, there is provided a particle analysis method including the steps of: detecting, by a laser light detector, part of laser light that is output from a light source; detecting fluorescence or scattered light or both the fluorescence and the scattered light, the fluorescence and the scattered light being emitted from particles irradiated with the laser light; and correcting, by a signal processing unit, a detection signal of the fluorescence or the scattered light or detection signals of both the fluorescence and the scattered light, based on a detection result in the laser light detector.

The step of correcting the detection signal or the detection signals may include correcting the detection signal or the detection signals in accordance with output fluctuations of the laser light detector.

In such a case, the step of correcting the detection signal or the detection signals may include correcting the detection signal or the detection signals by multiplying an output voltage by a value (Gain) that is set in accordance with magnitude of the output fluctuations of the laser light detector, the output voltage being acquired from the step of detecting fluorescence or scattered light or both the fluorescence and the scattered light.

Effects of the Invention

According to the present disclosure, it is possible to acquire detection data with high reliability without using high frequency superimposition. It should be noted that the effects described herein are not necessarily limited and any one of the effects described herein may be produced.

MODE(S) FOR CARRYING OUT THE INVENTION

Hereinafter, modes for carrying out the present disclosure will be described in detail with reference to the attached drawings. It should be noted that the present disclosure is not limited to the embodiments described later. Further, the description will be given in the following order.

1. First Embodiment (Example of particle analysis apparatus that corrects detection signal based on detection result by laser light detector)

2. Modified Example of First Embodiment (Example of particle analysis apparatus in which laser light detector is provided in light source drive control unit)

1. First Embodiment

[Overall Configuration of Apparatus]

Figure 1:
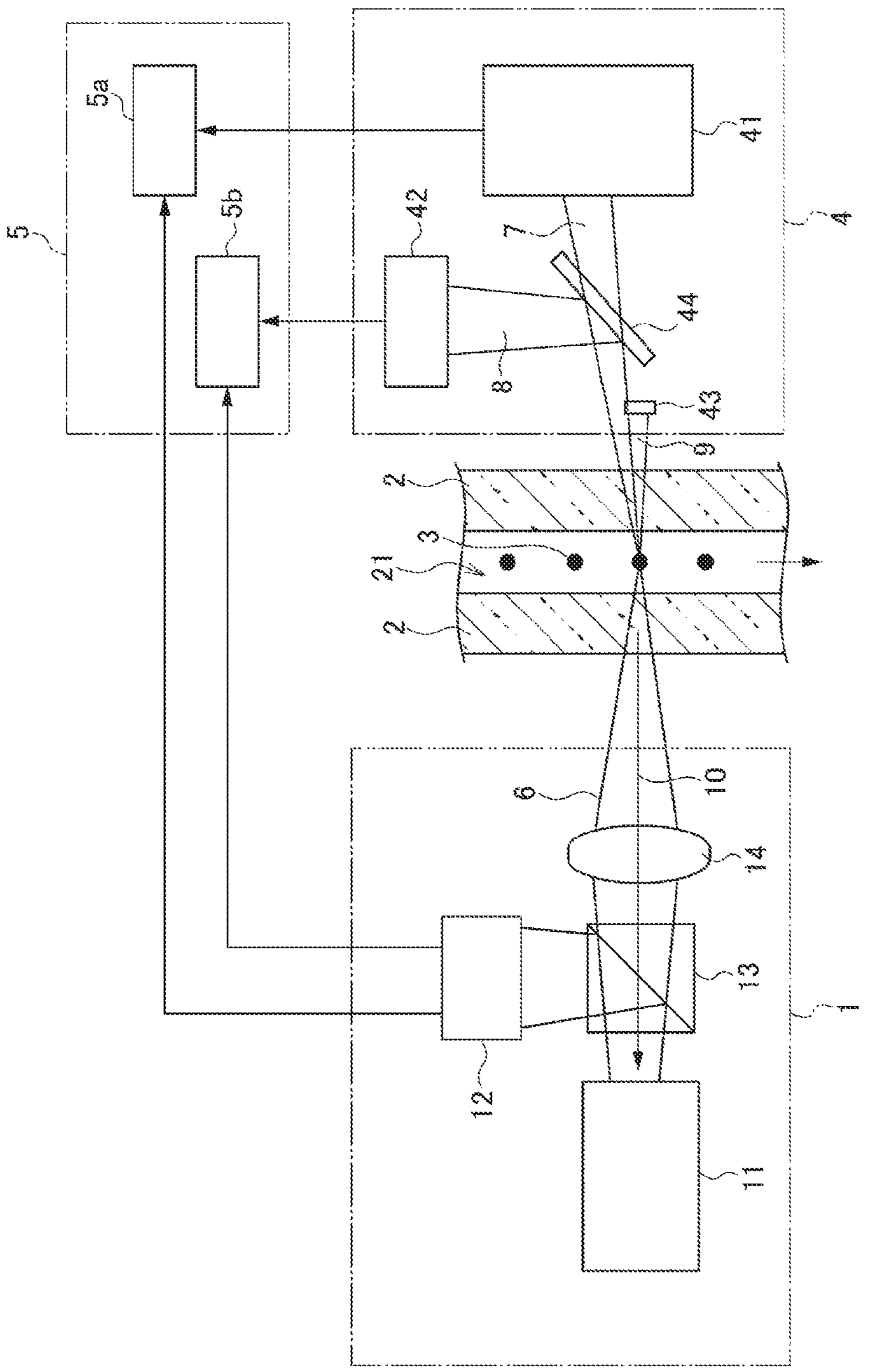
FIG. 1 is a diagram schematically showing a configuration of a particle analysis apparatus of a first embodiment of the present disclosure.

First, a particle analysis apparatus of a first embodiment of the present disclosure will be described using an example of a case where microparticles flowing within a flow path are detected. FIG. 1 is a diagram schematically showing a configuration of a particle analysis apparatus of this embodiment. As shown in FIG. 1, the particle analysis apparatus of this embodiment includes a light irradiation unit 1, a light detection unit 4, and a signal processing unit 5. The light irradiation unit 1 irradiates microparticles 3 with laser light 6. The light detection unit 4 detects fluorescence 7 or scattered light 8 that is emitted from the microparticles 3 irradiated with the light. The signal processing unit 5 processes a detection signal output from the light detection unit 4.

[Light Irradiation Unit 1]

The light irradiation unit 1 includes a laser 11 and a lens 14. The laser 11 generates the laser light 6. The lens 14 collects the laser light 6 toward the microparticles 3. Further, the light irradiation unit 1 includes a laser light detector 12 that detects the laser light 6, and has a configuration in which part of the laser light 6 output form the laser 11 is reflected on, for example, a beam splitter 13, to be input to the laser light detector 12. Here, the laser light detector 12 only needs to be capable of detecting output fluctuations of the laser light 6 that are generated in the order of several tens of μs, and a photodiode or the like can be used therefor.

[Microchip 2]

A microchip 2 includes a flow path 21 in which the microparticles 3 can flow. In the flow path 21, for example, a sample solution containing the microparticles 3 serving as detection target is introduced. The microchip 2 can be made of glass or various types of plastics (PP, PC, COP, PDMS, etc.). The material of the microchip 2 is not particularly limited, but is desirably a material having permeability with respect to the laser light 6 applied from the light irradiation unit 1 and having less optical errors.

The forming of the microchip 2 can be performed by wet etching or dry etching of a glass substrate or by nanoimprinting, injection molding, or machine processing of a plastic substrate. The substrate in which the flow path 21 and the like are formed can be sealed by a substrate that is made of the same material or a different material, to thus form the microchip 2.

[Microparticles 3]

The "microparticles 3" detected by the particle analysis apparatus of this embodiment widely include biologically-relevant microparticles such as cells, microbes, and ribosomes, or synthetic particles such as latex particles, gel particles, and particles for industrial use.

The biologically-relevant microparticles include chromosomes, ribosomes, mitochondria, organelles, and the like that form various cells. Further, the cells include plant cells, animal cells, hematopoietic cells, and the like. Moreover, the microbes include bacteria such as *Escherichia coli*, viruses such as tobacco mosaic viruses, fungi such as yeast, and the like. The biologically-relevant microparticles may include biologically-relevant polymers such as nucleic acids, proteins, and complexes thereof.

Examples of the particles for industrial use include particles made of organic polymeric materials, inorganic materials, metal materials, or the like. As the organic polymeric materials, polystyrene, styrene-divinylbenzene, polymethyl methacrylate, and the like can be used. Further, as the inorganic materials, glass, silica, magnetic materials, and the like can be used. As the metal materials, for example, gold colloid, aluminum, and the like can be used. It should be noted that those microparticles generally have spherical shapes, but may have non-spherical shapes. Further, the sizes, masses, and the like of those microparticles are also not particularly limited.

[Light Detection Unit 4]

The light detection unit 4 detects the fluorescence 7 or the scattered light 8 or detects both the fluorescence 7 and the scattered light 8, the fluorescence 7 and the scattered light 8 being emitted from the microparticles 3 irradiated with the laser light 6. For example, the light detection unit 4 includes a fluorescence detector 41 or a scattered light detector 42 or includes both the fluorescence detector 41 and the scattered light detector 42. Here, a photomultiplier tube (PMT) or the like can be used for the fluorescence detector 41, and a photodiode or the like can be used for the scattered light detector 42.

Further, the light detection unit 4 separates the fluorescence 7 and the scattered light 8 from light by a dichroic mirror 44, the light being emitted from the microparticles 3 and input to the light detection unit 4, and inputs the fluorescence 7 and the scattered light 8 to the fluorescence detector 41 and the scattered light detector 42, respectively. For the dichroic mirror 44 used in that case, for example, a dichroic mirror that causes the fluorescence 7 to pass therethrough and reflects the scattered light 8 can be used.

Further, the light detection unit 4 may include a zero-order-light removing member 43 that blocks a light component (zero order light 9), other than the fluorescence 7 and the scattered light 8, of the laser light 6 or the like being excitation light. For the zero-order-light removing member 43, a mask, an optical filter that selectively blocks specific light, and the like can be used, but the zero-order-light removing member 43 is not limited to those members. The zero-order-light removing member 43 only needs to be an optical member capable of blocking the zero order light 9. Further, the position in which the zero-order-light removing member 43 is disposed is also not particularly limited and may be in front of the fluorescence detector 41 and the scattered light detector 42.

[Signal Processing Unit 5]

The signal processing unit 5 corrects a detection signal of the fluorescence 7 or the scattered light 8 or detection signals of both the fluorescence 7 and the scattered light 8, based on a detection result in the laser light detector 12. The signal processing unit 5 includes a fluorescence signal processing unit 5*a*, a scattered light signal processing unit 5*b*, and the like so as to correspond to the detected light. As described above, in the case where high frequency superimposition is not performed, level fluctuations may occur in the output of the laser 11 due to return light 10, and a waveform may be disturbed. This disturbance has an influence also on the signal derived from the fluorescence 7 or the scattered light 8 that comes from the microparticles 3.

In this regard, the particle analysis apparatus of this embodiment corrects the detection signal of the fluorescence 7 in the fluorescence signal processing unit 5*a*, and corrects the detection signal of the scattered light 8 in the scattered light signal processing unit 5*b*, in accordance with output fluctuations of the laser light detector 12. Here, a method of correcting each detection signal is not particularly limited, but for example, the detection signals of the fluorescence 7 and the scattered light 8 can be corrected by multiplying an output voltage from the light detection unit 4 by a value (Gain) set in accordance with the magnitude of the output fluctuations of the laser light detector 12.

Further, the Gain can be a value obtained by dividing a reference voltage $V_{std}$ as an output voltage at any time by an output voltage $V_{out}$ at a time subsequent to the any time, as shown in the following expression 1, for example.

$$\text{Gain}=V_{std}/V_{out} \quad \text{[Math. 1]}$$

[Operation]

Next, description will be given on an operation of the particle analysis apparatus of this embodiment, that is, a method of analyzing the microparticles 3 using the particle analysis apparatus of this embodiment. In the particle analysis apparatus of this embodiment, a sample solution containing, for example, the microparticles 3 serving as detection target is introduced into the flow path 21 that is provided in the microchip 2. The laser light 6 output from the laser 11 is collected by the lens 14 or the like and is applied to the microparticles 3 that flow within the flow path 21 of the microchip 2.

At that time, part of the laser light 6 output from the laser 11 is separated by the beam splitter 13 or the like and is input to the laser light detector 12. The laser light detector 12 detects the intensity of the separated laser light 6 and outputs the result to the signal processing unit 5.

Further, after the zero order light is removed by the zero-order-light removing member 43, the light that is emitted from the microparticles 3 irradiated with the laser light 6 and that is input to the light detection unit 4 is separated into the fluorescence 7 and the scattered light 8 by the dichroic mirror 44 and then detected individually. Specifically, the fluorescence 7 that has passed through the dichroic mirror 44 is detected by the fluorescence detector 41, and the scattered light 8 that has been reflected on the dichroic mirror 44 is detected by the scattered light detector 42.

Figure 2:
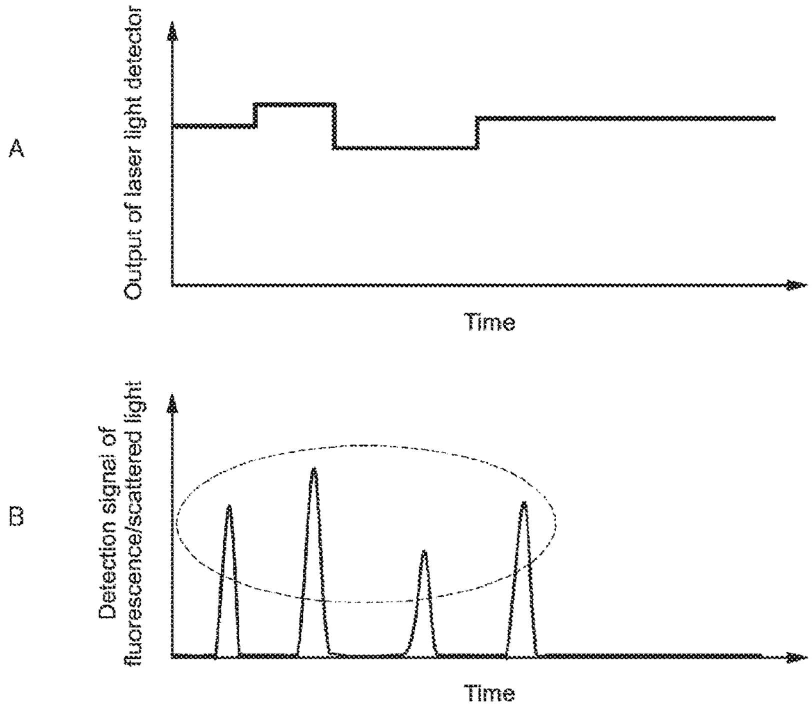
FIG. 2 Part A of FIG. 2 is a diagram showing output fluctuations of a laser light detector, and part B of FIG. 2 is a diagram showing an output signal from a light detection unit of a particle analysis apparatus in related art.
Figure 3:
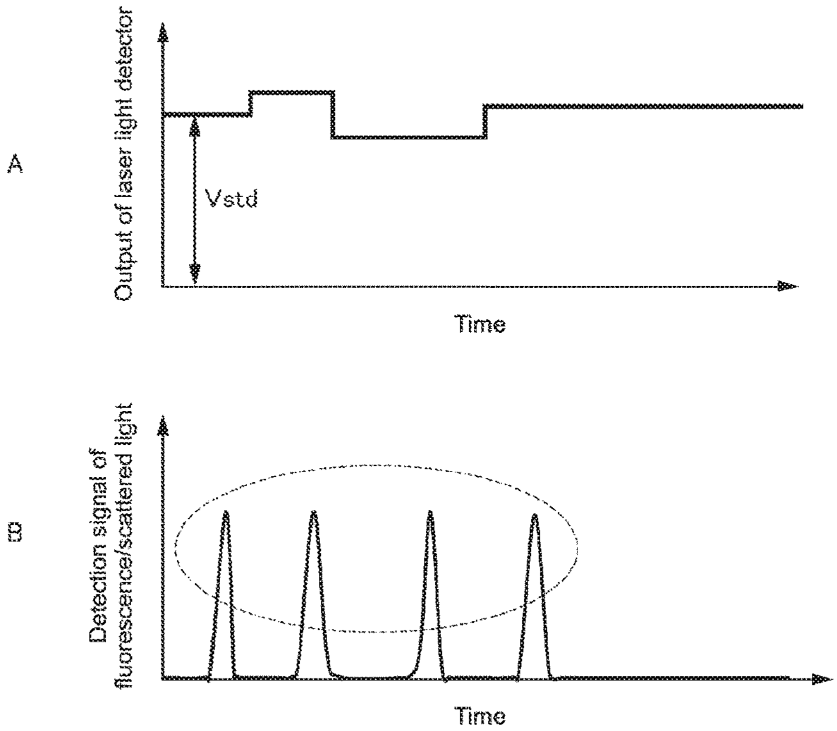
FIG. 3 Part A of FIG. 3 is a diagram showing output fluctuations of a laser light detector, and Part B of FIG. 3 is a diagram showing an output signal from a light detection unit of the particle analysis apparatus of this embodiment.

The detection results of the fluorescence detector 41 and the scattered light detector 42 are output to the signal processing unit 5. Specifically, the detection signal of the fluorescence detector 41 is output to the fluorescence signal processing unit 5*a* of the signal processing unit 5, and the detection signal of the scattered light detector 42 is output to the scattered light signal processing unit 5*b* of the signal processing unit 5. Part A of FIG. 2 is a diagram showing output fluctuations of the laser light detector, and part B of FIG. 2 is a diagram showing an output signal from a light detection unit of a particle analysis apparatus in related art. Part A of FIG. 3 is a diagram showing output fluctuations of the laser light detector, and part B of FIG. 3 is a diagram showing an output signal from the light detection unit of the particle analysis apparatus of this embodiment.

As shown in part A of FIG. 2 and part B of FIG. 2, in the particle analysis apparatus in related art, in which a correction corresponding to laser output fluctuations is not performed, variations in peak value are caused by the influence of the output fluctuations of the laser 11 (see a part surrounded by a broken line in part B of FIG. 2). In contrast to this, the particle analysis apparatus of this embodiment corrects the detection signal using the Gain that is set based on the output of the laser light detector 12. Therefore, as shown in part A of FIG. 3 and part B of FIG. 3, variations in signal can be suppressed, and the detection data with high reliability can be acquired (see a part surrounded by a broken line in part B of FIG. 3).

As described above in detail, in the particle analysis apparatus of this embodiment, the output fluctuations of the laser 11 are detected, and the detection signal is corrected based on the detection result. Therefore, it is possible to accurately detect the fluorescence or the scattered light or detect both the fluorescence and the scattered light without using high frequency superimposition. In such a manner, the particle analysis apparatus of this embodiment can acquire the detection data with high reliability without using high frequency superimposition. This makes it possible to use a laser whose maximum rating is low and to require no measures against unnecessary radiation.

It should be noted that FIG. 1 shows a configuration in which measurement is performed using a microchip, but the present disclosure is not limited thereto. A configuration using a flow cell, or the like is effective in all kinds of apparatuses causing problems of mode hopping noise and the like due to the output fluctuations of the laser. Further, FIG. 1 shows the apparatus that detects and corrects both the fluorescence and the scattered light, but the present disclosure is not limited thereto and may be a system that detects and corrects any one of the fluorescence and the scattered light.

2. Modified Example of First Embodiment

Figure 4:
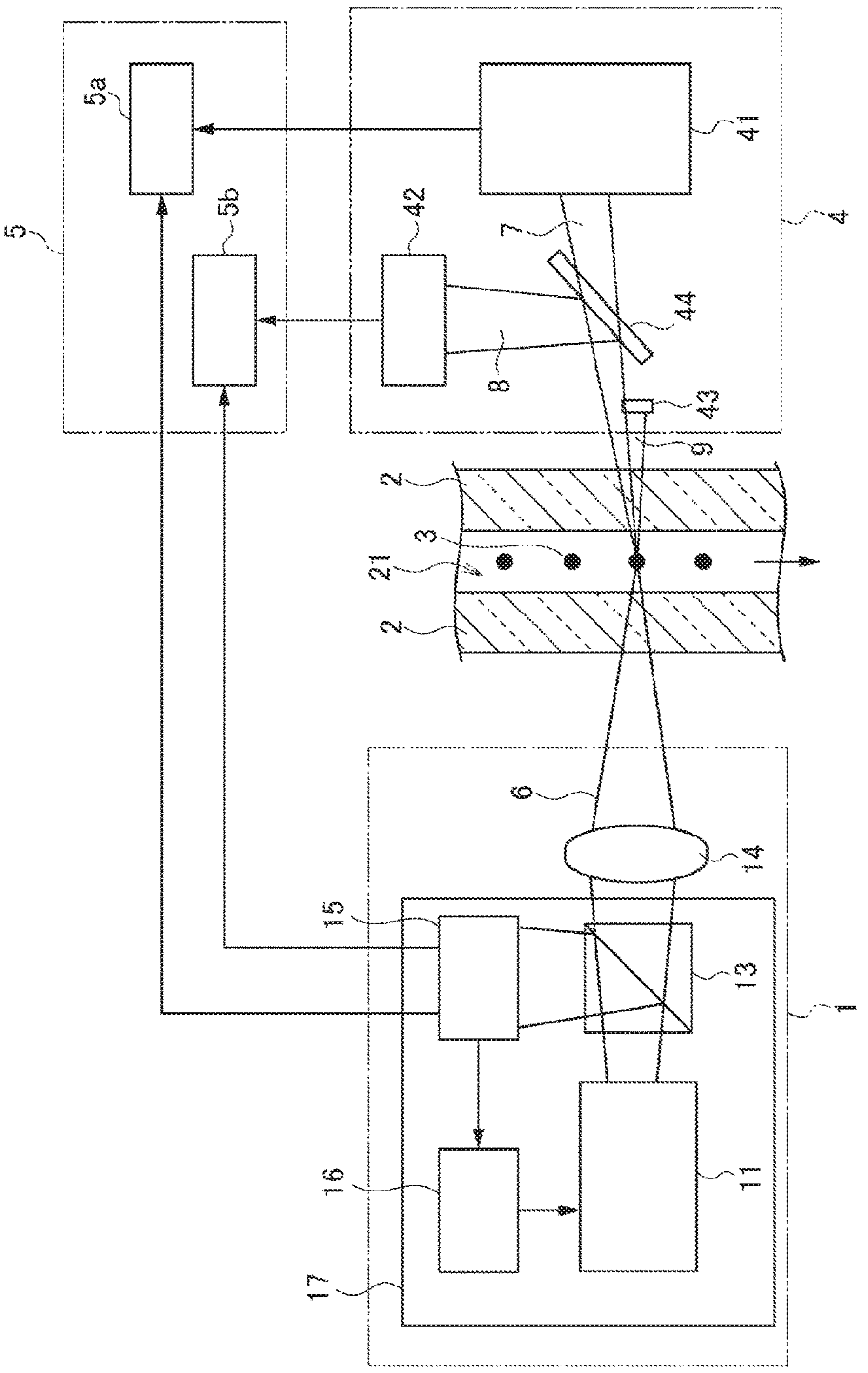
FIG. 4 is a diagram schematically showing a configuration of a particle analysis apparatus of a modified example of the first embodiment of the present disclosure.

Next, a particle analysis apparatus according to a modified example of the first embodiment of the present disclosure will be described. FIG. 4 is a diagram schematically showing a configuration of the particle analysis apparatus of this modified example. It should be noted that in FIG. 4, the same constituent elements as those of the particle analysis apparatus of the first embodiment described above are denoted by the same reference symbols, and detailed description thereof will be omitted.

As shown in FIG. 4, in the particle analysis apparatus of this modified example, a light source drive control unit 17 that adjusts output of the laser 11 is provided in the light irradiation unit 1. A detection result of a laser light detector 15 for feedback control in the light source drive control unit 17 is used to correct the detection signal. The light source drive control unit 17 of the particle analysis apparatus of this modified example includes a laser 11, a beam splitter 13, the laser light detector 15, a laser output adjustment unit 16, and the like. Part of laser light 6 output from the laser 11 is reflected on the beam splitter 13 and is detected by the laser light detector 15.

In the particle analysis apparatus of this modified example, the laser output adjustment unit 16 adjusts the output of the laser 11 based on the detection result in the laser light detector 15. Thus, it is possible to prevent the laser output level from fluctuating due to the influence of temperature or the like. This feedback control is normally performed in the order of several ms.

Further, in the particle analysis apparatus of this modified example, the detection result in the laser light detector 15 is output to the signal processing unit 5, and based on the detection result, a detection signal of the fluorescence or the scattered light or detection signals of both the fluorescence and the scattered light are corrected. This correction is performed for each data processing, for example.

In such a manner, using the detection result (output fluctuations) of the laser light detector 15 provided in the light source drive control unit 17 eliminates the necessity for separately providing a detector for correction. As a result, even if an apparatus, a component, or the like is not additionally provided, detection performance of fluorescence or scattered light can be improved, and detection data with high reliability can be acquired. It should be noted that a configuration, an operation, and an effect other than those described above in this modified example are the same as those in the first embodiment described above.

Further, the present disclosure can have the following configurations.

(1) A particle analysis apparatus, including:

a light irradiation unit that irradiates particles flowing within a flow path with laser light;

a light detection unit that detects fluorescence or scattered light or both the fluorescence and the scattered light, the fluorescence and the scattered light being emitted from the particles irradiated with the laser light; and a signal processing unit that processes a detection signal of the fluorescence or the scattered light or detection signals of both the fluorescence and the scattered light, the fluorescence and the scattered light being output from the light detection unit, the light irradiation unit including at least a light source that generates laser, and a laser light detector that detects part of laser light emitted from the light source, the signal processing unit correcting the detection signal of the fluorescence or the scattered light or the detection signals of both the fluorescence and the scattered light, based on a detection result in the laser light detector.

(2) The particle analysis apparatus according to (1), in which the signal processing unit corrects the detection signal or the detection signals in accordance with output fluctuations of the laser light detector.

(3) The particle analysis apparatus according to (1) or (2), in which the signal processing unit corrects the detection signal or the detection signals by multiplying an output voltage from the light detection unit by a value (Gain) that is set in accordance with magnitude of the output fluctuations of the laser light detector.

(4) The particle analysis apparatus according to any one of (1) to (3), in which the light irradiation unit includes a beam splitter that reflects the part of the laser light toward the laser light detector.

(5) The particle analysis apparatus according to any one of (1) to (4), in which the light irradiation unit includes a light source drive control unit that adjusts output of laser light based on a detection result in the laser light detector, the laser light being output from the light source.

(6) A particle analysis method, including the steps of:

detecting, by a laser light detector, part of laser light that is output from a light source;

detecting fluorescence or scattered light or both the fluorescence and the scattered light, the fluorescence and the scattered light being emitted from particles irradiated with the laser light; and correcting, by a signal processing unit, a detection signal of the fluorescence or the scattered light or detection signals of both the fluorescence and the scattered light, based on a detection result in the laser light detector.

(7) The particle analysis method according to (6), in which the step of correcting the detection signal or the detection signals includes correcting the detection signal or the detection signals in accordance with output fluctuations of the laser light detector.

(8) The particle analysis method according to (6) or (7), in which the step of correcting the detection signal or the detection signals includes correcting the detection signal or the detection signals by multiplying an output voltage by a value (Gain) that is set in accordance with magnitude of the output fluctuations of the laser light detector, the output voltage being acquired from the step of detecting fluorescence or scattered light or both the fluorescence and the scattered light.

DESCRIPTION OF SYMBOLS

1 light irradiation unit
2 microchip
3 microparticles
4 light detection unit
5 signal processing unit
**5*a*** fluorescence signal processing unit
**5*b*** scattered light signal processing unit
6 laser light
7 fluorescence
8 scattered light
9 zero order light
10 return light
11 laser
12, 15 laser light detector
13 beam splitter
14 lens
16 laser output adjustment unit
17 light source drive control unit
21 flow path
41 fluorescence detector
42 scattered light detector
43 zero-order-light removing member
44 dichroic mirror

The invention claimed is:

1. A particle analysis apparatus, comprising:

a light irradiation unit configured to irradiate particles that flow within a flow path with laser light;

a light detection unit configured to detect at least one of fluorescence light or scattered light, wherein the fluorescence light and the scattered light are emitted from the particles irradiated with the laser light; and a signal processing unit configured to process a detection signal of the at least one of the fluorescence light or the scattered light, wherein the detection signal of the at least one of the fluorescence light or the scattered light is output from the light detection unit based on the detection, wherein the light irradiation unit includes at least:

a light source configured to generate the laser light; and a laser light detector configured to detect a part of the laser light emitted from the light source, wherein the signal processing unit is further configured to correct, the detection signal of the at least one of the fluorescence light or the scattered light, based on a detection result of the laser light detector and based on output fluctuations of the laser light detector.

2. The particle analysis apparatus according to claim 1, wherein the signal processing unit is further configured to correct the detection signal of the at least one of the fluorescence light or the scattered light based on multiplication of an output voltage from the light detection unit and a gain that is set in accordance with magnitude of the output fluctuations of the laser light detector.

3. The particle analysis apparatus according to claim 1, wherein the light irradiation unit includes a beam splitter configured to reflect the part of the laser light toward the laser light detector.

4. The particle analysis apparatus according to claim 1, wherein the light irradiation unit includes a light source drive control unit configured to adjust output of the laser light based on the detection result in the laser light detector, and wherein the laser light is output from the light source.

5. A particle analysis method, comprising:

detecting, by a laser light detector, a part of laser light that is output from a light source;

detecting at least one of fluorescence light or scattered light, wherein the fluorescence light and the scattered light are emitted from particles irradiated with the laser light; and correcting, by a signal processing unit, a detection signal of the at least one of the fluorescence light or the scattered light, based on a detection result of the laser light detector and output fluctuations of the laser light detector.

6. The particle analysis method according to claim 5, wherein the correction of the detection signal of the at least one of the fluorescence light or the scattered light includes multiplying an output voltage by a gain that is set in accordance with magnitude of the output fluctuations of the laser light detector, and wherein the output voltage is acquired from the detection of the at least one of the fluorescence light or the scattered light.

* * * * *